(12) United States Patent
Park (10) Patent No.: US 9,817,492 B2
(45) Date of Patent: Nov. 14, 2017

(54) WIRELESS ELECTRONIC PEN SET

(71) Applicant: Inchul Park, Daegu (KR)

(72) Inventor: Inchul Park, Daegu (KR)

( * ) Notice: Subject to any disclaimer, the term of this patent is extended or adjusted under 35 U.S.C. 154(b) by 0 days.

(21) Appl. No.: 15/411,808

(22) Filed: Jan. 20, 2017

(65) Prior Publication Data

US 2017/0269721 A1 Sep. 21, 2017

(30) Foreign Application Priority Data

Mar. 18, 2016 (KR) .................. 10-2016-0032644

(51) Int. Cl.
*G06F 3/0354* (2013.01)
*G06F 3/038* (2013.01)

(52) U.S. Cl.
CPC ........ *G06F 3/03545* (2013.01); *G06F 3/0383* (2013.01); *G06F 3/03547* (2013.01); *G06F 2203/0384* (2013.01)

(58) Field of Classification Search
None
See application file for complete search history.

(56) References Cited

U.S. PATENT DOCUMENTS

| | | | |
|---|---|---|---|
| 7,955,017 B2 * | 6/2011 | Lapstun ................. | B43K 7/005 345/179 |
| 8,172,474 B2 * | 5/2012 | Dickover ............. | B43K 23/002 24/3.13 |
| 2006/0250380 A1 * | 11/2006 | Oliver ................. | G06F 3/03545 345/179 |
| 2009/0046058 A1 * | 2/2009 | Antos ..................... | G08C 17/02 345/156 |
| 2014/0253468 A1 * | 9/2014 | Havilio ............... | G06F 3/03545 345/173 |
| 2015/0153845 A1 * | 6/2015 | Chang ................. | G06F 3/03545 345/179 |

FOREIGN PATENT DOCUMENTS

| | | |
|---|---|---|
| KR | 10-2003-0017924 A | 3/2003 |
| KR | 10-0769981 B1 | 10/2007 |
| KR | 10-2010-0129676 A | 12/2010 |

* cited by examiner

*Primary Examiner* — William Boddie
*Assistant Examiner* — David Lee
(74) *Attorney, Agent, or Firm* — KORUS Patent, LLC; Seong Il Jeong (57) ABSTRACT

A wireless electronic pen set in association with a terminal device having a display is disclosed, the set comprising: a wireless electronic pen; a wireless stick communicating with the pen in a wireless manner, wherein the stick is physically and removably secured to the terminal device and communicates with the device in a wired manner, wherein the wireless electronic pen includes: a touch input unit to receive a touch input from a user; a first wireless communication unit to communicate with the stick; and a controller to enable the touch input to be sent to the device via the wireless communication unit, wherein the stick includes: a second wireless communication unit to communicate with the pen; and a connector electrically connected to the device, wherein the touch input is transferred via the second wireless communication unit and the connector to the device.

4 Claims, 5 Drawing Sheets

WIRELESS ELECTRONIC PEN SET

CROSS-REFERENCE TO RELATED APPLICATION

This application claims the benefit of Korea patent application No. 10-2016-0032644 filed on Mar. 18, 2016, the entire content of which is incorporated herein by reference for all purposes as if fully set forth herein.

BACKGROUND

Field of the Present Disclosure

The present disclosure relates to a wireless electronic pen set, and, more particularly, a wireless electronic pen set wherein an electronic pen is associated with various terminals such as a smart phone, a notebook, IPTV, HMD terminal, vehicle touch display, etc. via a wireless stick coupled thereto.

Discussion of Related Art

Today's portable devices are equipped with complex functions such as photographing and video shooting, playback of music files and video files, games, reception of broadcasts, and wireless Internet support, and are implemented as a comprehensive multimedia device.

Accordingly, portable devices have been developed in a new form in terms of hardware and software in order to enhance portability and convenience while satisfying the needs of users.

The electronic pen is used as auxiliary means to conveniently control the functions of various portable devices. The portable device senses input by the electronic pen and controls various functions of the portable device according to the sensed input.

However, although the electronic pen combined with a portable device can be used for various purposes, nowadays it is used as auxiliary means of input, but there is no use for other purposes.

On the other hand, recently, the spread of e-books and the like is increasing. When an e-book is read at a high speed, continuous hand-touch causes inconvenience for the user.

Furthermore, when the user has to touch the touch screen of the terminal at a long distance, there is a problem that it is inconvenient to use.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure is to provide a wireless electronic pen set wherein an electronic pen is associated with various terminals such as a smart phone, a notebook, IPTV, HMD terminal, vehicle touch display, etc. via a wireless stick coupled thereto.

Furthermore, the present disclosure is to provide a wireless electronic pen set wherein a wireless electronic pen emits a fragrance when using a pen tip to comfort the user's mind and body.

Furthermore, the present disclosure is to provide a wireless electronic pen set wherein a wireless electronic pen functions as voice input means.

Furthermore, the present disclosure is to provide a wireless electronic pen set wherein a wireless electronic pen induces stability of the mind and body by emitting a fragrance by the pen tip sensor unit inside the pen.

Furthermore, the present disclosure is to provide a wireless electronic pen set wherein a wireless electronic pen provides memory stick functionality as needed to store important information.

In addition, the present disclosure is to provide a wireless electronic pen set wherein a wireless electronic pen indicates a direction of a touch and allows the user to precisely input the touch according to his or her intention.

In addition, the present disclosure is to provide a wireless electronic pen set wherein the vibration due to the vibration element in association with contents may provide the user with the haptic sensing.

Furthermore, the present disclosure is to provide a wireless electronic pen set wherein the function of recognizing and transmitting a fingerprint may be provided with the wireless electronic pen wherein a fingerprint recognition function is embodied by the touch panel of the pen.

Moreover, the present disclosure is to provide a wireless electronic pen set wherein it is possible using a wireless electronic pen set to display and select a zoom-in/zoom-out function, a pointing function, a direction key function, a volume control, a TV channel control, a color adjustment, etc. for a smart phone, a notebook, IPTV, HMD terminal, vehicle touch display, etc. via a wireless stick coupled thereto.

In one aspect, there is provided an elongate wireless electronic pen comprising: a touch input unit to receive a touch input from a user; a pen tip to stimulate an external device; a display unit to display information; a wireless communication unit to communicate with the external device; a controller to enable a direction of the touch input to be displayed on the display unit and to enable the touch input to be sent to the device via the wireless communication unit, wherein the wireless pen has an elongate accommodation space defined therein to receive a further electronic pen therein, wherein the further electronic pen is removable from the wireless pen, wherein the wireless pen has a retainer to removably retain the further electronic pen in the accommodation space.

In one embodiment, the wireless pen further includes a sensor to detect interaction between the pen tip and the display of the device; and a fragrance emitter configured to emit fragrance based on the detected interaction, wherein the controller is configured to receive the detected interaction and thus, enable the emitter to emit fragrance.

In another aspect, there is provided a wireless electronic pen set in association with a terminal device having a display, the set comprising: a wireless electronic pen; a wireless stick communicating with the pen in a wireless manner, wherein the stick is physically secured to the terminal device and communicates with the device in a wired manner, wherein the stick is removable from the device, wherein the wireless electronic pen includes: a touch input unit to receive a touch input from a user; a pen tip to stimulate the display of the device; a first wireless communication unit to communicate with the stick; and a controller to enable the touch input to be sent to the device via the wireless communication unit, wherein the stick includes: a second wireless communication unit to communicate with the pen; and a connector electrically connected to the device, wherein the touch input is transferred via the second wireless communication unit and the connector to the device.

In one embodiment, the touch input includes a scrolling input.

In one embodiment, the stick further include a memory unit.

Other features and aspects may be apparent from the following detailed description, the drawings, and the claims.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

For simplicity and clarity of illustration, elements in the figures are not necessarily drawn to scale. The same reference numbers in different figures denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Furthermore, the use of "may" when describing embodiments of the present disclosure refers to "one or more embodiments of the present disclosure."

Figure 1:
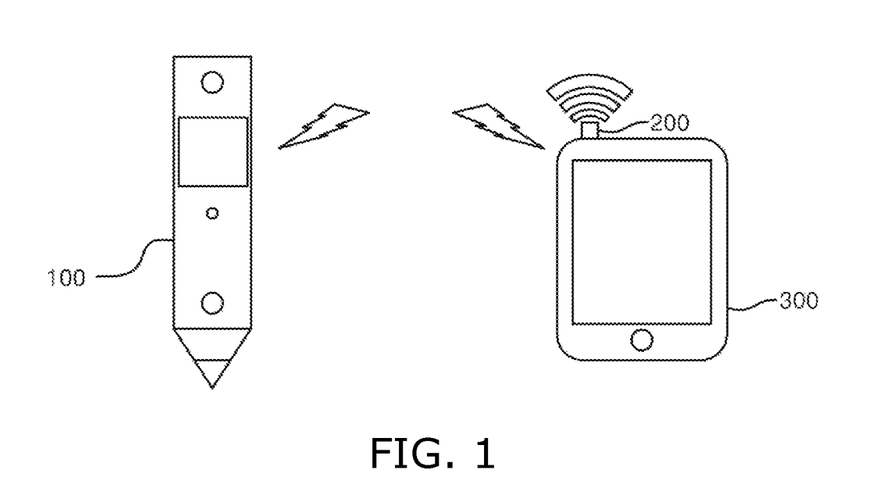
FIG. 1 to FIG. 3 illustrate a schematic view of a wireless electronic pen set for a smart phone, a notebook, IPTV, HMD terminal, vehicle touch display, etc. in accordance with embodiments of the present disclosure.
Figure 2:
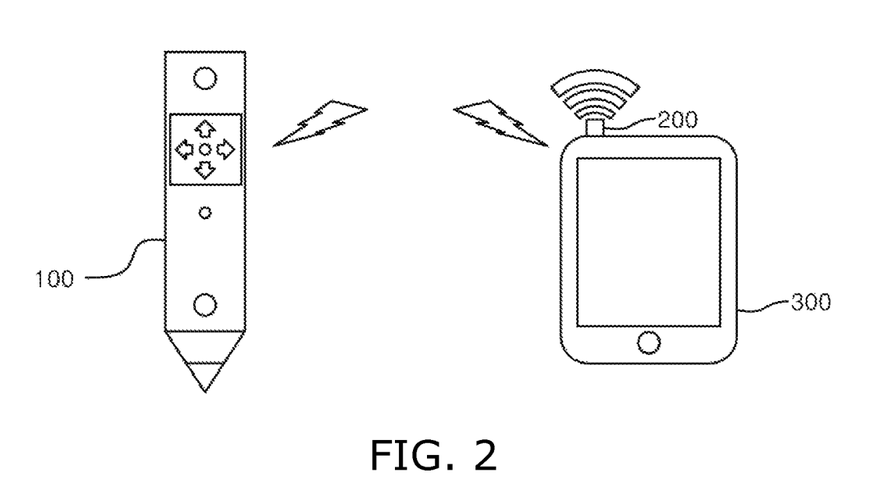
Figure 3:
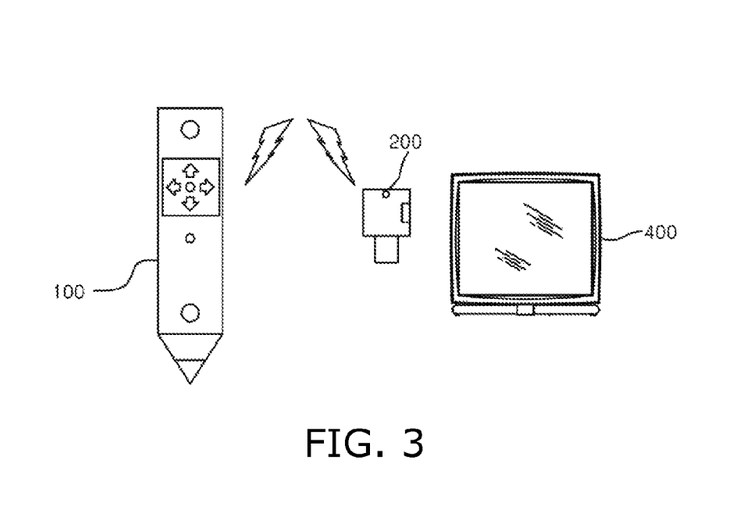

FIG. 1 to FIG. 3 illustrate a schematic view of a wireless electronic pen set for a smart phone, a tablet, a PDA, a netbook, a notebook, IPTV, HMD terminal, vehicle touch display, various another terminals, etc. in accordance with embodiments of the present disclosure.

Referring to FIG. 1, a wireless electronic pen set according to an embodiment of the present disclosure include a wireless electronic pen 100 and a stick 200 wirelessly communicating with the pen 100, wherein the stick 200 is connected to a terminal 300 or notebook 400 using a USB type connector.

In this connection, the wireless electronic pen 100 according to the embodiment of the present disclosure performs various functions including a general wireless pointing function or various controlling functions. In particular, the screen of the portable terminal operates in association with the operation of the wireless electronic pen 100 according to the present disclosure embodiment.

Furthermore, referring to FIG. 2 or FIG. 3, the wireless electronic pen 100 according to the embodiment of the present disclosure can be used not only for a mobile terminal but also for a wireless terminal such as a notebook, an HMD terminal, and a car terminal. Further, the terminal includes a smart phone, a tablet, a PDA, a netbook, a notebook, etc. The present disclosure is not limited thereto.

Furthermore, the operation of the wireless electronic pen 100 may be associated with the operation of the touch screen of the portable terminal in a real time manner, so that the pen 100 can perform the scrolling control and the pointing function for the touch screen of the portable terminal.

Furthermore, as shown in FIG. 1, in one embodiment, the display screen of the wireless electronic pen 100 and the display screen of the terminal 300 according to the embodiment of the present disclosure may have the same input configuration, that is, the input position correspondence. Further, as shown in FIG. 2, the display screen of the wireless electronic pen 100 according to the embodiment of the present disclosure may have a direction indication function.

Hereinafter, the wireless electronic pen 100 according to an embodiment of the present disclosure will now be described in detail.

Figure 4:
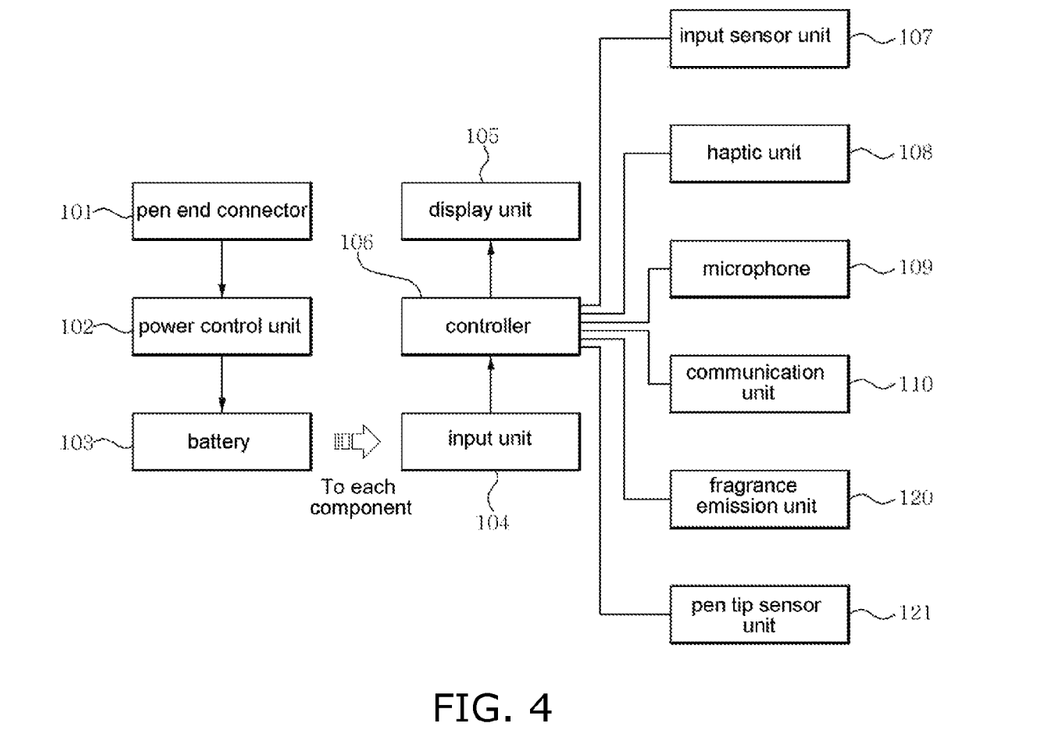
FIG. 4 is a block diagram of a wireless electronic pen according to an embodiment of the present disclosure.
Figure 5:
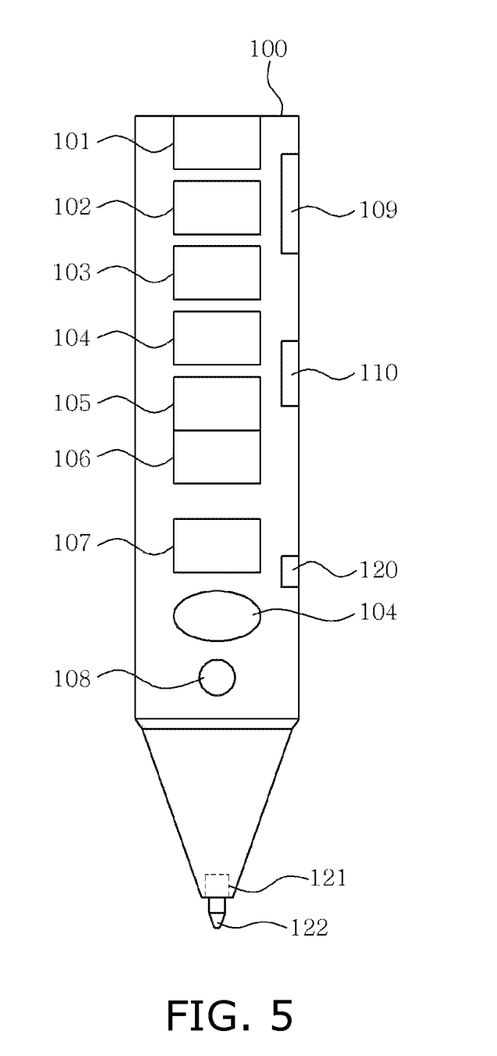
FIG. 5 is a diagram schematically showing positions of components included in a wireless electronic pen according to an embodiment of the present disclosure.

FIG. 4 is a block diagram of a wireless electronic pen according to an embodiment of the present disclosure. FIG. 5 is a diagram schematically showing positions of components included in a wireless electronic pen according to an embodiment of the present disclosure.

The wireless electronic pen 100 in wireless communication with the stick 200 connected, in a wired manner, to with a terminal 300 or notebook 400 may include: a main body 100, and following various components incorporated in the main body 100: an input unit 104 for receiving a touch input of a user; a pen tip 122 for inputting information to the terminal; a display unit 105 for displaying information; a wireless communication unit 110 for wirelessly communicating with the stick 200; a control unit 106 to enable transmitting the touch information of the input unit to the stick 200 through the wireless communication unit 110 and displaying the input direction of the input unit 104 on the display unit 105.

In this connection, as shown in FIG. 2 and FIG. 3, the direction indication unit may send the input direction to the control unit 110. The input direction may include left, right, up and down directions. The present disclosure is not limited thereto.

Furthermore, the controller or control unit 106 recognizes the touch direction from the input of the input unit 104. The pen 100 further includes an input sensor unit 107 as needed to recognize the touch direction more accurately. The controller or control unit 106 may send the recognized direction to the input sensor unit 107.

The pen may further include the pen tip sensor unit 121 for sensing the operation of the pen tip 122; and a fragrance diffusing unit 120 for diffusing fragrance.

When the activation of the pen tip 122 is sensed from the pen tip sensor unit 121, the control unit 106 controls the perfume emitting part 120 to emit a fragrance.

In this connection, the fragrance emission unit 120 has a valve, is configured to open and close the valve, and emits liquid spray such as perfume. Further, a motor may be additionally provided to be driven so that the perfume can spread evenly.

Such a fragrance is emitted when the user uses the pen tip 122, thereby stimulating olfactury so that the mind and body can be stabilized.

In addition, the control unit 106 receives scroll or touch input through the input unit 104, transmits the scroll or touch input to the stick 200, to perform a wireless navigation or pointing function.

Further, if necessary, the microphone unit 109 can be additionally provided so that voice input can be performed at the time of lecture or presentation. The voice signal is output through the speaker of the terminal 300 or the notebook 400 connected, in a wired manner, to the stick 200 under the control of the control unit 106. Therefore, although the user speaks with a small voice, the voice can be amplified in a desired magnitude throughout the space.

The input unit 104 may be implemented by a touch panel using various touch techniques such as a resistance film approach, an electrostatic or capacitive approach, a capacitive and pressure approach, a switch input approach (analog or digital approach), a surface ultrasonic approach, and a piezo effect approach.

The control unit 106 transmits the signal received from the input unit 104 to the terminal 300 or the USB type stick 200 through the wireless communication unit 110.

In the terminal 300 or the notebook computer 400, the touch signal transmitted through the wireless communication unit 110 is analyzed on the operating system (OS) to control the screen association between the pen 100 and the terminal 300 or the notebook computer 400. Furthermore, the pen may perform navigation or pointing function or wireless remote control function.

In addition, the controller 106 may control functions of the wireless electronic pen 100 in association with the contents executed in the terminal 300.

Specifically, the controller 106 may activate a haptic function of the wireless electronic pen 100 in association with the contents executed in the terminal 300. The controller 106 may control a display function of the wireless electronic pen 100 in association with the contents executed in the terminal 300.

The pen tip portion 122 may be used in connection with the touch panel of the terminal 300, and may be of an electrostatic type or EMR type. When the electrostatic or capacitive type is applied, the sensor unit 121 for detecting the presence or absence of touch of the electrostatic or capacitive pen tip may be provided to notify the control unit 106 of touch presence/absence, intensity of the touch.

The power control unit 102 enables charging the battery 103 and displaying the status of the battery 103 through the USB-type pen end connector 101.

The battery 103 may be recharged but may be replaced as needed.

The display unit 105 may include a LED and/or a LCD unit, display the same image as that displayed on the terminal 300, and/or display the power state and the touch state information with a simple indicator.

Further, the control unit 106 is communicatively connected to an external physical electronic character structure through the wireless communication unit 110 or an earphone terminal, if necessary, and can enable the physical electronic character structure to express a facial expression or emotion of the character using an input of the input unit 104. Furthermore, if necessary, the controller 106 may enable the physical electronic character structure to express a vocal expression or emotion of the character using an input of the input unit 104.

Furthermore, the physical electronic character structure may be produced separately. Alternatively, the physical electronic character structure may be combined with a further wireless electronic pen according to the embodiment of the present disclosure.

Hereinafter, the stick 200 in association with the wireless electronic pen according to an embodiment of the present disclosure will be described in detail.

Figure 6:
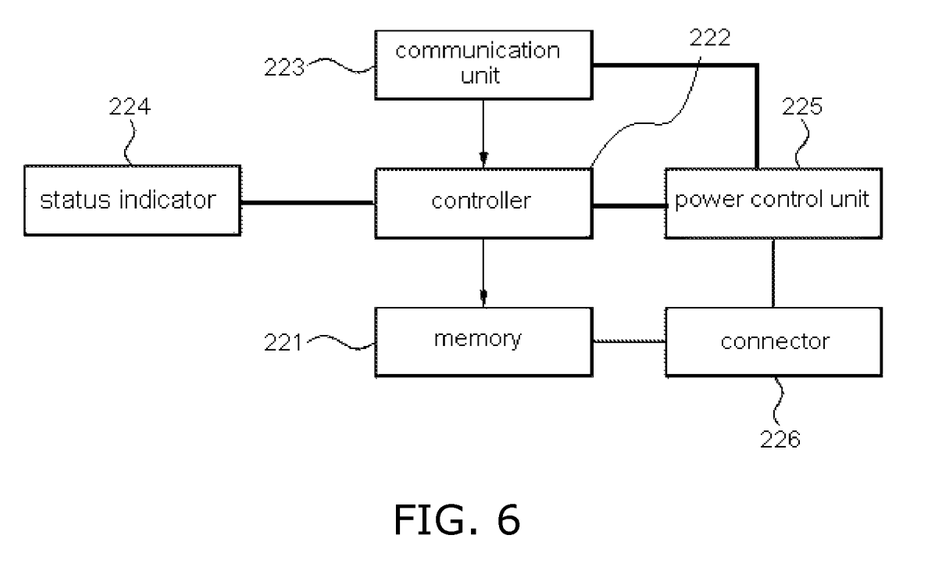
FIG. 6 is a block diagram of a wireless stick associated with a wireless electronic pen according to an embodiment of the present disclosure.
Figure 7:
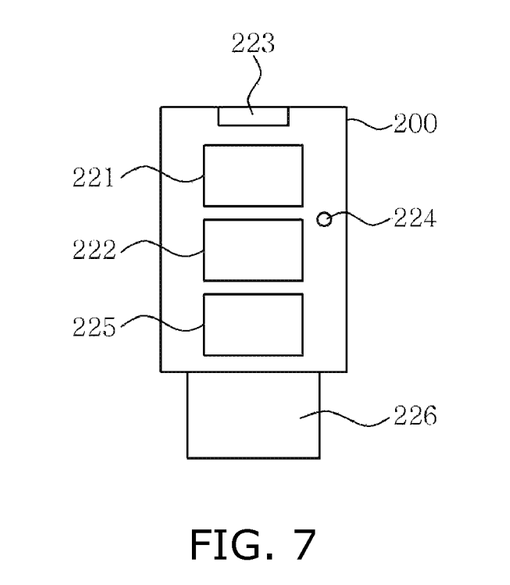
FIG. 7 is a view schematically showing positions of components incorporated in a wireless stick according to the embodiment of the present disclosure.

FIG. 6 is a block diagram of a wireless stick associated with a wireless electronic pen according to an embodiment of the present disclosure. FIG. 7 is a view schematically showing positions of components incorporated in a wireless stick according to the embodiment of the present disclosure.

Referring to FIG. 6 and FIG. 7, a wireless stick associated with a wireless electronic pen according to an embodiment of the present disclosure includes a stick communication unit 223, a stick control unit 222, a stick memory 221, a stick power control unit 225, a status display 224, and a stick connector 226.

The stick communication unit 223 may communicate wirelessly with the wireless electronic pen 100 and may be connected and secured to the terminal 300 or the notebook computer 400 through the stick connector 226 of the USB type.

The stick control unit 222 transmits information received from the wireless electronic pen 100 to the terminal 300 or the notebook 400 and transmits information transmitted from the terminal 300 or the notebook 400 to the wireless electronic pen 100.

Information can be stored in the memory 221 which may function as a USB memory stick if necessary.

The stick power control unit 225 receives power from the terminal 300 or the notebook 400 via the USB stick type connector 226 and supplies the power to the respective units.

Furthermore, the stick control unit 225 can enable displaying of the power status or the communication status through the status display unit 224.

The status display unit 224 can be variously formed. In one example, it may be embodied as a simple LED or LCD indictor.

In one embodiment of the present disclosure, the user controls the input unit 104 in association with the terminal 300 to enable an imaging unit in the terminal 300 to execute an imaging operation, as needed.

Figure 8:
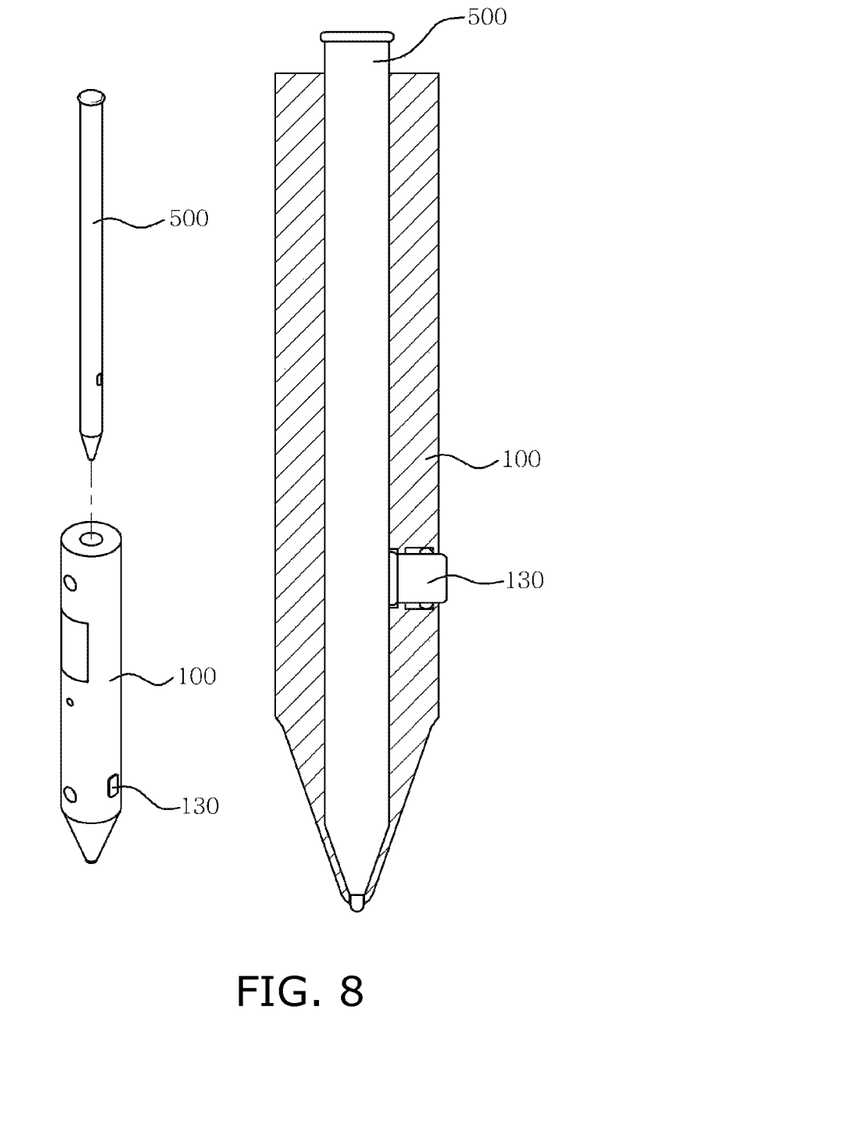
FIG. 8 is a view showing a state in which a wireless electronic pen receives a further wireless electronic pen therein according to an embodiment of the present disclosure.

FIG. 8 is a view showing a state in which a wireless electronic pen receives a further wireless electronic pen according to an embodiment of the present disclosure Referring to FIG. 8, the wireless electronic pen 100 according to the embodiment of the present disclosure can be used in combination with a further wireless electronic pen 500. The further wireless electronic pen 500 may be housed in the wireless electronic pen 100. In one example, the further wireless electronic pen 500 may include a conventional stylus for a smart phone.

For example, the interior of the wireless electronic pen 100 provides a storage space for the further wireless electronic pen 500, and, thus, the further wireless electronic pen 500 may be inserted into and removed from the storage space defined in the wireless electronic pen 100 as needed.

In this connection, the user may select the further wireless electronic pen 500 and the wireless electronic pen 100 depending on the desired function or a finger size and a desired gripping feel. For example, the wireless electronic pen 100 may have a larger diameter than that of the conventional wireless electronic pen 500 such that the user may graph the former more easily.

In addition, if necessary, a fixing mechanism or retainer 130 may be added to allow the further wireless electronic pen 500 to be more firmly secured to the wireless electronic pen 100. Such a fixation may be implemented variously. In one embodiment, the fixing mechanism 130 may be embodied as a spring. In another embodiment of the present disclosure, it may be implemented by enhancing the frictional force.

In accordance with the present disclosure, the electronic pen is associated with various terminals such as a smart phone, a notebook, IPTV, HMD terminal, vehicle touch display, etc. via a wireless stick coupled thereto to control the operation of the terminals including the navigation or pointing function on the screen of the terminals.

Furthermore, in accordance with the present disclosure, the wireless electronic pen emits a fragrance when using a pen tip to comfort the user's mind and body.

Furthermore, in accordance with the present disclosure, the wireless electronic pen functions as voice input means such as a microphone.

Furthermore, in accordance with the present disclosure, the wireless electronic pen induces stability of the mind and body by emitting a fragrance via the pen tip sensor unit inside the pen.

Furthermore, in accordance with the present disclosure, the wireless electronic pen provides memory stick functionality as needed to store important information.

In addition, in accordance with the present disclosure, the wireless electronic pen indicates a direction of a touch and allows the user to precisely input the touch according to his or her intention.

In addition, in accordance with the present disclosure, the vibration due to the vibration element in association with specific portions in the contents displayed in the terminal may provide the user with the haptic sensing.

Furthermore, in accordance with the present disclosure, the function of recognizing and transmitting a fingerprint may be provided with the wireless electronic pen wherein a fingerprint recognition function is embodied by the touch panel of the pen.

Moreover, in accordance with the present disclosure, it is possible using the wireless electronic pen set to display and select a zoom-in/zoom-out function, a pointing function, a direction key function, a volume control, a TV channel control, a color adjustment, etc. for a smart phone, a notebook, IPTV, HMD terminal, vehicle touch display, etc. via a wireless stick coupled thereto.

Various function or operations of the control unit or controller of the disclosure may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as, but not limited to, source code, compiled code, interpreted code, executable code, static code, dynamic code, and the like. Such a computer-readable medium may include any tangible non-transitory medium for storing information in a form readable by one or more computers, such as, but not limited to, read only memory (ROM); random access memory (RAM); magnetic disk storage media; optical storage media; a flash memory, etc.

The term "computer-readable medium" may include any medium that is capable of storing, encoding, or carrying instructions for execution by the machine and that cause the machine to perform any one or more of the techniques of the present disclosure, or that is capable of storing, encoding, or carrying data structures used by or associated with such instructions. Non-limiting, machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., Electrically Programmable Read-Only Memory (EPROM), or Electrically Erasable. Programmable Read-Only Memory (EEPROM)) and flash memory devices; magnetic disks, such as internal hard disks and removable disks; magneto-optical disks; and CD-ROM and DVD-ROM disks.

While aspects of the present invention have been described with reference to exemplary embodiments, it is to be understood that the aspects of the invention are not limited to the disclosed exemplary embodiments. The scope of the following claims is to be accorded the broadest interpretation so as to encompass all such modifications and equivalent structures and functions.

The above description is not to be taken in a limiting sense, but is made merely for the purpose of describing the general principles of exemplary embodiments, and many additional embodiments of this disclosure are possible. It is understood that no limitation of the scope of the disclosure is thereby intended. The scope of the disclosure should be determined with reference to the Claims. Reference throughout this specification to "one embodiment," "an embodiment," or similar language means that a particular feature, structure, or characteristic that is described in connection with the embodiment is included in at least one embodiment of the present disclosure. Thus, appearances of the phrases "in one embodiment," "in an embodiment," and similar language throughout this specification may, but do not necessarily, all refer to the same embodiment.

What is claimed is:

1. An elongate wireless electronic pen comprising:
a touch input unit to receive a touch input from a user;
a pen tip to stimulate an external device;
a display unit to display information;
a wireless communication unit to communicate with the external device;
a controller to enable a direction of the touch input to be displayed on the display unit and to enable the touch input to be sent to the device via the wireless communication unit,
wherein the wireless pen has an elongate accommodation space defined therein to receive a further electronic pen therein, wherein the further electronic pen is removable from the wireless pen,
wherein the wireless pen has a retainer to removably retain the further electronic pen in the accommodation space.

2. The wireless pen of claim 1, further includes:
a sensor to detect interaction between the pen tip and the display of the device; and
a fragrance emitter configured to emit fragrance based on the detected interaction, wherein the controller is configured to receive the detected interaction and thus, enable the emitter to emit fragrance.

3. A wireless electronic pen set in association with a terminal device having a display, the set comprising:
a wireless electronic pen;
a wireless stick communicating with the pen in a wireless manner, wherein the stick is physically secured to the terminal device and communicates with the device in a wired manner, wherein the stick is removable from the device,
wherein the wireless electronic pen includes:
a touch input unit to receive a touch input from a user;
a pen tip to stimulate the display of the device;
a display unit to display information;
a first wireless communication unit to communicate with the stick; and
a controller to enable a direction of the touch input to be displayed on the display unit and to enable the touch input to be sent to the device via the wireless communication unit,
wherein the stick includes:
a second wireless communication unit to communicate with the wireless electronic pen; and
a connector electrically connected to the device, wherein the touch input is transferred via the second wireless communication unit and the connector to the device so that the display of the terminal device operates in association with the touch input of the wireless electronic pen,
wherein the wireless pen has an elongate accommodation space defined therein to receive a further electronic pen therein, wherein the further electronic pen is removable from the wireless pen,
wherein the wireless pen has a retainer to removably retain the further electronic pen in the accommodation space.

4. The set of claim 3, wherein the touch input includes a scrolling input.

* * * * *